US00PP31624P2

(12) United States Plant Patent

Klemm et al.

(10) Patent No.: US PP31,624 P2
(45) Date of Patent: Mar. 31, 2020

(54) *DAHLIA* PLANT NAMED 'KLEDH18110'

(50) Latin Name: ***Dahlia* sp.**
Varietal Denomination: KLEDH18110

(71) Applicant: Klemm+Sohn GmbH & Co. KG, Stuttgart (DE)

(72) Inventors: Nils Klemm, Stuttgart (DE); Maike Boxriker, Schwäbisch Gmünd (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/501,866

(22) Filed: Jun. 20, 2019

(30) Foreign Application Priority Data

Apr. 10, 2019 (CA) ..... PBR 199748

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./231
CPC ..... A01H 5/02; A01H 6/14
See application file for complete search history.

*Primary Examiner* — Annette H Para
(74) *Attorney, Agent, or Firm* — James M. Weatherly; Cochran Freund & Young LLC

(57) ABSTRACT

A new *Dahlia* plant particularly distinguished by red flowers with a yellow center, dark green foliage, and a compact, semi-upright habit, is disclosed.

1 Drawing Sheet

Genus and species: *Dahlia* sp.
Variety denomination: 'KLEDH18110'.

CROSS REFERENCE TO RELATED APPLICATIONS

This application claims the benefit of priority under 35 U.S.C. 119 (f) to the application for Canadian Plant Breeders Rights which was filed for the instant plant variety on Apr. 10, 2019, Application number 19-9748.

BACKGROUND OF THE NEW PLANT

The present invention comprises a new and distinct variety of *Dahlia*, botanically known as *Dahlia* sp., and hereinafter referred to by the variety name 'KLEDH18110'. 'KLEDH18110' originated from an open-pollination in September 2014 in Stuttgart, Germany between the proprietary female *Dahlia* variety 'DH-2014-1084' (unpatented) and an unknown male *Dahlia* variety.

The seeds from the open-pollination were sown and plants were grown in a greenhouse for evaluation, where an individual plant designated 'KLEDH18110' was selected from the group in May 2015 in Stuttgart, Germany. In May 2015, 'KLEDH18110' was first vegetatively propagated by cuttings. 'KLEDH18110' was found to reproduce true to type in successive generations of asexual propagation via terminal cuttings in Stuttgart, Germany, Tenerife, and Kenya.

SUMMARY

The following are the most outstanding and distinguishing characteristics of this new variety when grown under normal horticultural practices in Stuttgart, Germany.

1. Red flowers with a yellow center;
2. Dark green foliage; and
3. A compact, semi-upright growth habit.

DESCRIPTION OF THE PHOTOGRAPH

This new *Dahlia* plant is illustrated by the accompanying photograph of a plant approximately 5 months old and grown outdoors in Stuttgart, Germany. The photograph was taken in August 2017 and shows the flowers and foliage. The colors shown are as true as can be reasonably obtained by conventional photographic procedures.

DESCRIPTION OF THE NEW VARIETY

The following detailed descriptions set forth the distinctive characteristics of 'KLEDH18110'. The data which define these characteristics were collected from asexual reproductions carried out in Latina, Italy. Data was collected in May 2019 on 15 week-old plants potted in week 5 and grown in a glass greenhouse. Color references are to The R.H.S. Colour Chart of The Royal Horticultural Society of London (R.H.S.), 5$^{th}$ edition (2007).

Classification:
*Family.*—Asteraceae.
*Botanical.*—*Dahlia* sp.
*Common.*—*Dahlia.*
*Designation.*—'KLEDH18110'.

Parentage:
*Female parent.*—'DH-2014-1084' (unpatented).
*Male parent.*—Unknown.

Plant:
*Plant and growth habit.*—Compact, semi-upright, free basal branching, and inflorescences held above the foliar plane.
*Height.*—31.0 cm.
*Diameter.*—25.0 cm.
*Propagation.*—Terminal cuttings.
*Time to produce a rooted young plant.*—8 to 9 weeks.

*Root description*.—Fine, white, RHS 155A.
*Rooting habit*.—Freely branching and moderately dense.

Lateral branches:
*Length*.—29.0 cm.
*Diameter*.—0.6 cm.
*Internode length*.—6.2 cm.
*Aspect*.—Outwardly spreading.
*Strength*.—Strong.
*Texture*.—Smooth.
*Color*.—RHS 146A.

Foliage/leaves:
*Arrangement*.—Leaves are opposite, pinnately lobed.
*Length*.—8.4 cm.
*Width*.—7.1 cm.
*Shape*.—Pinnate.
*Apex*.—Acute.
*Base*.—Acute.
*Margin*.—Sinuate.
*Venation pattern*.—Dichotomous.
*Venation color* (*both surfaces*).—RHS 138A.
*Texture* (*both upper and lower surfaces*).—Smooth.
*Immature leaf color*.—Upper surface: RHS 137B. Lower surface: RHS 147B.
*Mature leaf color*.—Upper surface: RHS 147A. Lower surface: RHS 147B.
*Petioles*.—Length: 1.5 cm. Diameter: 0.4 cm. Texture (both upper and lower surfaces): Smooth. Color: Upper surface: RHS 144B. Lower surface: RHS 144B.

Buds:
*Height*.—0.5 cm.
*Diameter*.—0.9 cm.
*Shape*.—Circular.
*Color*.—RHS 144B.

Inflorescence:
*Appearance and arrangement*.—Daisy-eyed double inflorescences held above the foliar plane.
*Fragrance*.—Present, sweet.
*Time to flower*.—In the winter, about 3 months after planting; in the summer, about 2 months after planting.
*Post-production longevity*.—Plants flower continuously from spring through autumn.
*Inflorescence diameter*.—6.0 cm.
*Inflorescence depth*.—3.0 cm.
*Disc diameter*.—1.1 cm.
*Receptacle height*.—0.6 cm.
*Receptacle diameter*.—1.5 cm.
*Receptacle color*.—RHS 141B.

Ray florets:
*Quantity per inflorescence*.—40 arranged in about 3 to 4 whorls.
*Length*.—3.2 cm.
*Width*.—1.7 cm.
*Shape*.—Oval.
*Apex*.—Rounded.
*Base*.—Rounded.
*Margin*.—Entire.
*Aspect*.—Semi-upright.
*Texture*.—Upper surface: Smooth. Lower surface: Weakly rugose.
*Color, immature*.—Upper surface: RHS 45B. Lower surface: RHS 46B.
*Color, mature*.—Upper surface: RHS 45A. Lower surface: RHS 46B.

Disc florets:
*Quantity per inflorescence*.—About 25.
*Length*.—About 0.9 cm.
*Diameter*.—0.2 cm.
*Shape*.—Tubular.
*Texture* (*both the upper and lower surfaces*).—Smooth.
*Color, immature*.—Upper surface: RHS 1B. Lower surface: RHS 1D.
*Color, mature*.—Upper surface: RHS 3B. Lower surface: RHS 1D.

Phyllaries:
*Quantity per inflorescence*.—52.
*Length*.—1.5 cm.
*Width*.—0.7 cm.
*Shape*.—Elliptic.
*Apex*.—Acute.
*Base*.—Acute.
*Margin*.—Entire.
*Texture* (*both upper and lower surfaces*).—Smooth.
*Color*.—Upper surface: RHS 146C. Lower surface: RHS 146C.

Peduncles:
*Length, terminal peduncle*.—13.5 cm.
*Length, axillary peduncle*.—15.0 cm.
*Diameter*.—0.3 cm.
*Aspect*.—Semi-upright.
*Strength*.—Strong.
*Texture*.—Smooth.
*Color*.—RHS 144A.

Reproductive organs:
*Androecium*.—Present on ray florets and disc florets. Quantity per floret: 2. Filament length: 0.6 cm. Filament color: RHS 1B. Anther shape: Long lanceolate. Anther length: 0.4 cm. Anther color: RHS 17A. Pollen amount: Medium. Pollen color: RHS 9A.
*Gynoecium*.—Present on ray florets and disc florets. Quantity per floret: 1. Pistil length: 0.7 cm. Style length: 0.4 cm. Style color: RHS 13B. Stigma shape: Lanceolate. Stigma color: RHS 14B. Ovary color: RHS 1B.

Fruit and seed set: No fruit and seed set observed.

Disease and pest/insect resistance: No disease and pest/insect resistance observed.

COMPARISON WITH PARENTAL LINE AND KNOWN VARIETY

'KLEDH18110' is a distinct variety of *Dahlia* and is distinguished from its female parent as follows. Whereas 'KLEDH18110' has red flowers and good branching, female parental line 'DH-2014-1084' has orange flowers and medium branching.

'KLEDH18110' is a distinct variety of *Dahlia* and is most similar to the commercial *Dahlia* variety 'Dalaya Amba' (also known as 'KLEDH18010'). Differences between the varieties are as follows. Whereas 'KLEDH18110' has red flowers with a yellow center, 'Dalaya Amba' has red flowers with a black center. Additionally, 'Dalaya Amba' flowers later than 'KLEDH18110'.

We claim:

1. A new and distinct variety of *Dahlia* plant designated 'KLEDH18110' as illustrated and described herein.

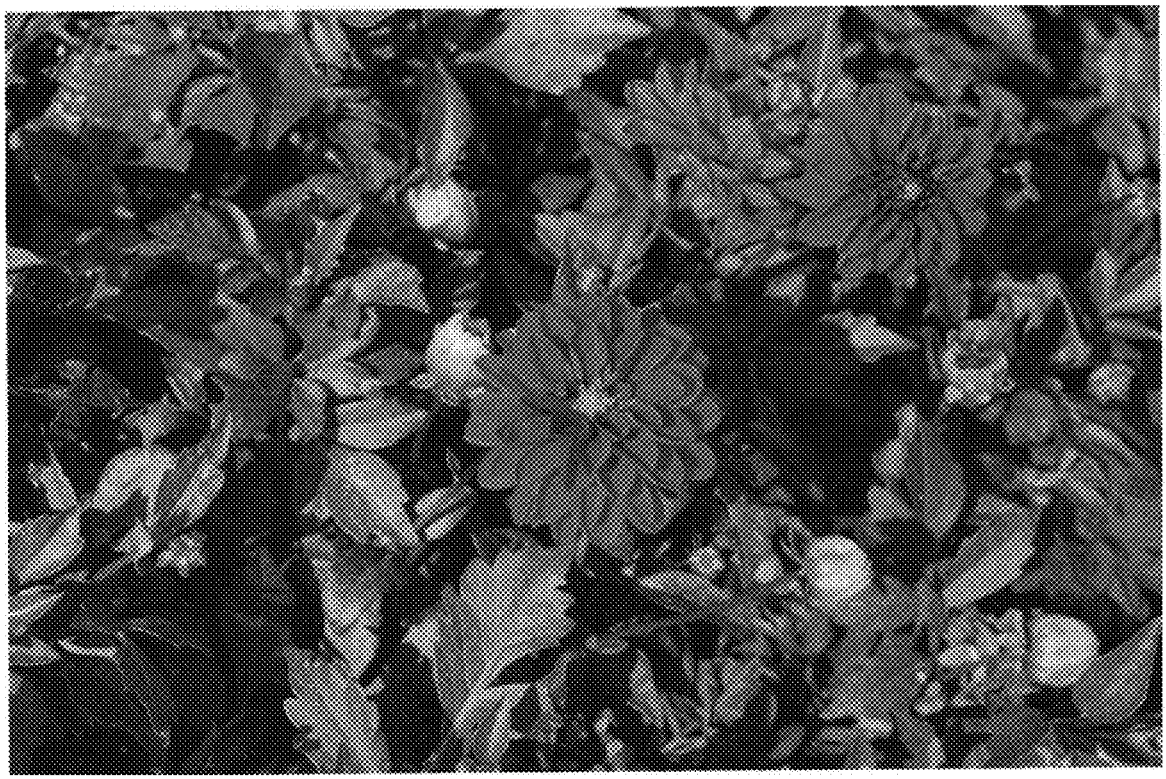

* * * * *